United States Patent
Jones et al.

(10) Patent No.: US 9,689,816 B2
(45) Date of Patent: Jun. 27, 2017

(54) XRF ANALYZER ACTIVATION SWITCH

(71) Applicant: Moxtek, Inc., Orem, UT (US)

(72) Inventors: Vincent Floyd Jones, Cedar Hills, UT (US); Daniel N. Paas, Spanish Fork, UT (US); Brad Harris, Farmington, UT (US)

(73) Assignee: Moxtek, Inc., Orem, UT (US)

( * ) Notice: Subject to any disclaimer, the term of this patent is extended or adjusted under 35 U.S.C. 154(b) by 123 days.

(21) Appl. No.: 14/886,342

(22) Filed: Oct. 19, 2015

(65) Prior Publication Data

US 2016/0054243 A1 Feb. 25, 2016

Related U.S. Application Data

(63) Continuation-in-part of application No. 14/821,350, filed on Aug. 7, 2015.

(60) Provisional application No. 62/039,767, filed on Aug. 20, 2014, provisional application No. 62/095,302, filed on Dec. 22, 2014.

(51) Int. Cl.
*G01N 23/223* (2006.01)

(52) U.S. Cl.
CPC ... *G01N 23/223* (2013.01); *G01N 2223/0766* (2013.01); *G01N 2223/301* (2013.01)

(58) Field of Classification Search
CPC ........... G01N 23/223; G01N 2223/076; G01N 2223/301
USPC ..................................... 378/43–50
See application file for complete search history.

(56) References Cited

U.S. PATENT DOCUMENTS

| | | | |
|---|---|---|---|
| 7,889,335 B2 * | 2/2011 | Durst | G01J 3/02 356/326 |
| 2008/0192889 A1 | 8/2008 | Rohde et al. | |
| 2009/0064276 A1 * | 3/2009 | Dugas | G01N 35/00732 726/2 |
| 2010/0150307 A1 | 6/2010 | Godzins | |
| 2010/0226476 A1 | 9/2010 | Pesce et al. | |
| 2011/0191108 A1 | 8/2011 | Friedlander | |
| 2012/0236989 A1 | 9/2012 | Hardman | |
| 2013/0022166 A1 | 1/2013 | Drummy | |
| 2013/0321793 A1 | 12/2013 | Hamilton et al. | |
| 2014/0201033 A1 | 7/2014 | Crain et al. | |
| 2014/0301530 A1 | 10/2014 | Failla, Jr. et al. | |

FOREIGN PATENT DOCUMENTS

KR 10-2008-0098103 A 11/2008

* cited by examiner

*Primary Examiner* — Courtney Thomas
(74) *Attorney, Agent, or Firm* — Thrope, North & Western, LLP

(57) ABSTRACT

The invention includes various electronic devices for avoiding or minimizing XRF analyzer user fatigue. In one embodiment, the XRF analyzer can include a finger sensor for activating an XRF analysis. In another embodiment, the XRF analyzer can include a finger tap switch for activating the XRF analysis. In another embodiment, the XRF analyzer can include a microphone for activating the XRF analysis by receipt of a verbal command. Additional benefits of some embodiments include improving XRF analysis safety and avoiding XRF analyzer theft.

19 Claims, 1 Drawing Sheet

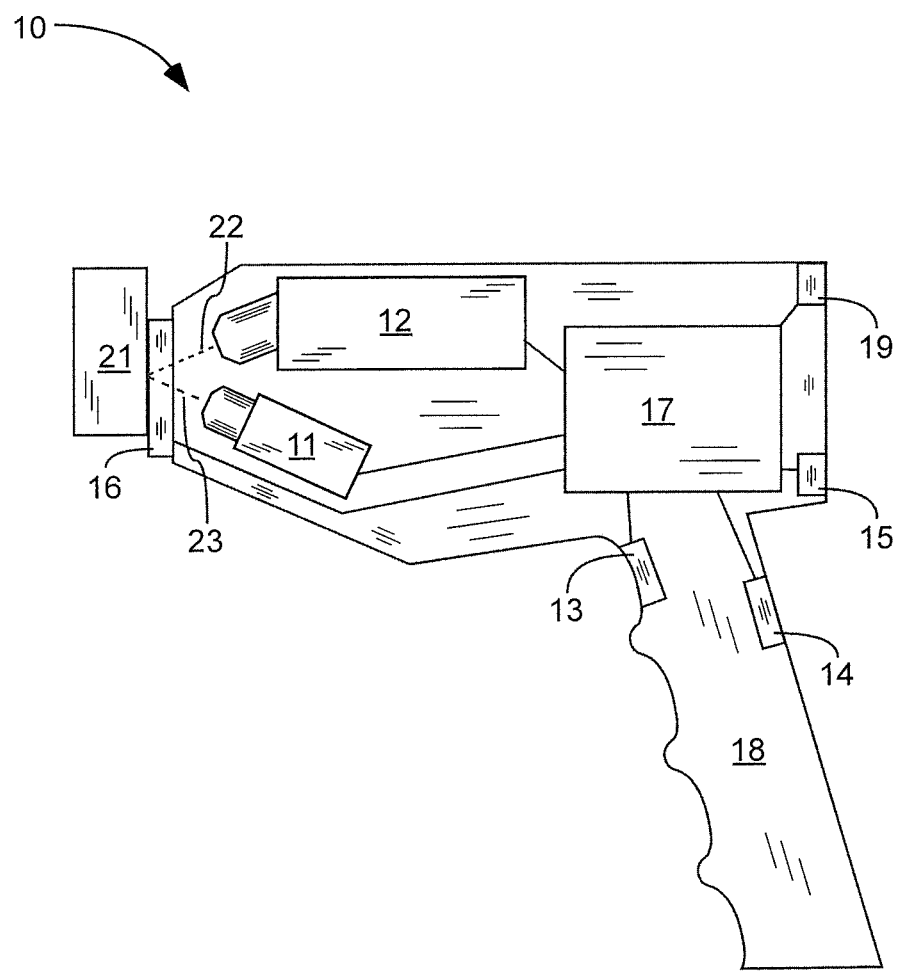

XRF ANALYZER ACTIVATION SWITCH

CLAIM OF PRIORITY

This is a continuation-in-part of U.S. patent application Ser. No. 14/821,350, filed on Aug. 7, 2015, which claims priority to U.S. Provisional Patent Application No. 62/039,767, filed on Aug. 20, 2014, both of which are hereby incorporated herein by reference in their entirety. This claims priority to U.S. Provisional Patent Application No. 62/095,302, filed on Dec. 22, 2014, which is hereby incorporated herein by reference in its entirety.

FIELD OF THE INVENTION

The present application is related generally to XRF Analyzers.

BACKGROUND

X-ray florescence (XRF) analyzers typically perform an XRF analysis while a user presses a plunger-type trigger. It can be fatiguing for the user to press and hold the trigger during the entire analysis. Another possible problem of XRF analyzers is inadvertent emission of x-rays if the trigger is accidently pressed. Another concern is that a person who is not trained in XRF analysis might use the XRF analyzer, which could result in personal injury or equipment damage. XRF analyzers can be expensive. Theft of XRF analyzers can be another concern to XRF analyzer owners.

Some or all of the above description may also be applicable to laser-induced breakdown spectroscopy (LIBS) analysis tools, x-ray diffraction (XRD) analysis, and Raman spectroscopy tools.

SUMMARY

It has been recognized that it would be advantageous to avoid or minimize fatigue of an x-ray florescence (XRF) analyzer user, improve XRF analysis safety, and avoid XRF analyzer theft. The present invention is directed to various embodiments of XRF analyzers that satisfy these needs. Each embodiment may satisfy one, some, or all of these needs.

The XRF analyzer can comprise an x-ray source configured to emit x-rays towards a sample, an x-ray detector configured to receive fluoresced x-rays emitted from the sample, an activation switch, and an electronic processor. The activation switch can be electrically coupled to the electronic processor to activate an XRF analysis. The XRF analysis can include the electronic processor causing the x-ray source to emit x-rays towards the sample, the x-ray detector to receive the fluoresced x-rays emitted from the sample, and analysis of the fluoresced x-rays.

In one embodiment, the activation switch can include a finger sensor. The finger sensor can comprise a temperature sensor, a photo sensor, a pressure sensor, a capacitive sensor, and/or a radio-frequency identification (RFID) reader configured to receive a signal from an RFID tag on a user of the XRF analyzer. In another embodiment, the activation switch can include a finger tap switch capable of activating the XRF analysis by a tap from a finger of the user on the finger tap switch. In another embodiment, the activation switch can include a microphone capable of receiving a verbal command from the user to activate the XRF analysis upon receipt of the verbal command. In another embodiment, the activation switch can include a combination of the finger sensor, the finger tap switch, and/or the microphone.

BRIEF DESCRIPTION OF THE DRAWINGS

FIG. 1 is a schematic cross-sectional side view of a XRF analyzer, in accordance with an embodiment of the present invention.

DETAILED DESCRIPTION

As illustrated in FIG. 1, an x-ray fluorescence (XRF) analyzer 10 is shown comprising an x-ray source 12, an x-ray detector 11, an activation switch 13, and an electronic processor 17. The x-ray source 12 can be configured to emit x-rays 22 towards a sample 21. The x-ray detector 11 can be configured to receive fluoresced x-rays 23 emitted from the sample 21.

The activation switch 13 can be electrically coupled to the electronic processor 17 and operable to activate an XRF analysis. The electronic processor 17 can be electrically coupled to the x-ray source 12 and the x-ray detector 11. The XRF analysis can include (1) the electronic processor 17 causing the x-ray source 12 to emit x-rays 22 towards the sample 21; (2) the x-ray detector 11 receiving the fluoresced x-rays 23 emitted from the sample 21; and (3) analysis of the fluoresced x-rays 23. The analysis of the fluoresced x-rays 23 can mean that the x-ray detector 11 amplifies a signal based on the fluoresced x-rays 23 and the electronic processor 17 analyzes the amplified signal to determine material composition of the sample 21. The analysis of the fluoresced x-rays 23 can also mean that the x-ray detector 11 sends an amplified or unamplified signal to the electronic processor 17 which emits the signal through a wire or wirelessly to another device (e.g. external computer) for analysis of material composition of the sample 21.

The activation switch 13 can include various types of activation devices that can minimize fatigue of an x-ray XRF analyzer 10 user. For example, the activation switch 13 can include a finger sensor, a finger tap switch, and/or a microphone.

The finger sensor can comprise a temperature sensor, a photo sensor, a pressure sensor, a capacitive sensor, and/or a radio-frequency identification (RFID) reader configured to receive a signal from an RFID tag on a user of the XRF analyzer. Thus, the XRF analysis can be activated by the temperature sensor sensing heat of a finger of the user, the photo sensor sensing the finger due to a decrease in light, the pressure sensor sensing pressure of the finger of the user, the capacitive sensor sensing a change in capacitance due to the finger of the user, and/or the RFID reader sensing presence of the RFID tag on the user. The RFID tag can be attached to the user by a ring, glove, wrist strap, or other convenient device. (The temperature sensor, the photo sensor, the pressure sensor, the capacitive sensor, and the RFID reader associated with the finger sensor can be a primary or finger temperature sensor, a primary or finger photo sensor, a primary or finger pressure sensor, a primary or finger capacitive sensor and a primary or finger RFID reader, respectively.)

Each of these different types of finger sensors has different advantages and disadvantages, and thus one type might be better for one application and another type for another application. For example, a capacitive sensor might be preferred because it would be less likely to cause activation of the XRF analysis by a non-human object pressed against the activation switch 13. As another example, the photo sensor or pressure sensor might be preferred over the capacitive sensor if the user likely would wear gloves while using the XRF analyzer 10. It might also be preferred to combine multiple of these devices, such as for example the pressure sensor and the capacitive sensor in order to avoid undesirable activation of the XRF analysis. The RFID reader could be combined with any of the other sensors to improve safety by avoiding unauthorized use of the XRF analyzer 10—only the user could use the XRF analyzer 10 as long as the user kept the RFID tag in a secure location. Also, the RFID reader could help to discourage or avoid theft because the thief would have to steal both the XRF analyzer 10 and the RFID tag in order to operate the unit. This theft of both could be difficult if the XRF analyzer 10 and the RFID tag were stored in separate locations.

The finger sensor can activate the XRF analysis by the user's finger touching the activation switch 13 or by merely approaching the activation switch 13. A required touch can avoid undesired activation or continuation of the XRF analysis. The finger sensor can be a pressure sensor that is configured to activate the XRF analysis only by force within a certain range that is typical of force applied by a finger, thus further avoiding undesired activation of the XRF analysis. For example, the pressure sensor can be configured to activate the XRF analysis by the finger of the user pressing the pressure sensor with a pressure of between 10 and 30 newtons of force. On the other hand, allowing a mere approach of the user's finger for activation can reduce user fatigue. The finger sensor can be configured to activate the XRF analysis by the finger of the user approaching, but not touching, the finger sensor. For example, the finger sensor can have a photo sensor and can be configured to activate the XRF analysis when the user's finger approaches less than 6 millimeters of the finger sensor. Another way of avoiding user fatigue is for the activation switch 13 to include a finger tap switch. Thus, XRF analysis can be activated by a tap of the user's finger rather than requiring the user to continuously hold the activation switch. For example the activation switch 13 can include a temperature sensor, a photo sensor, a pressure sensor, and/or a capacitive sensor that activate the XRF analysis with a tap of the user's finger rather than requiring the user to continuously hold the activation switch. The finger tap switch can be configured to activate the XRF analysis by multiple taps, such as a double tap for example (similar to use of a computer mouse). Multiple taps can reduce the chance of undesired activation an XRF analysis. Each tap (whether single, double, or more) can have a short required duration. This required duration can be user controlled, similar to a computer mouse. For example, each tap can have a required duration of less than 0.1 second in one aspect, less than 0.25 second in another aspect, less than one second in another aspect, or less than three seconds in another aspect.

Use of a microphone, capable of receiving a verbal command from a user to activate the XRF analysis, as the activation switch 13, can avoid the chance of undesired activation of the XRF analysis because the XRF analysis would not be accidently activated by setting the XRF analyzer 10 on top of another device. A microphone might also be preferable if the user will wear gloves during the analysis. The microphone can also be useful for discouraging theft by requiring a password or voice recognition of the user's voice for XRF analysis. The microphone could also be configured to receive a command from the user to stop the analysis. The activation switch 13 can include the microphone plus the finger sensor and/or the finger tap switch to further avoid undesired activation of the XRF analysis, thus improving XRF analysis safety.

Addition of a hand sensor 14 can also avoid undesired activation or continuation of the XRF analysis. The hand sensor 14 can be located at a handle 18 of the XRF analyzer 10 and spaced apart from the activation switch 13. The hand sensor 14 can be electrically coupled to the electronic processor 17, the finger switch 13, or both. The hand sensor 14 can comprise a temperature sensor, a photo sensor, a pressure sensor, a capacitive sensor, and/or an RFID reader configured to receive a signal from an RFID tag on the user of the XRF analyzer 10. (The temperature sensor, the photo sensor, the pressure sensor, the capacitive sensor, and the RFID reader associated with the hand sensor can be a secondary or hand temperature sensor, a secondary or hand photo sensor, a secondary or hand pressure sensor, a secondary or hand capacitive sensor and a secondary or hand RFID reader, respectively.) Thus, the hand sensor combined with the activation switch 13 (microphone, finger sensor, and/or the finger tap switch) can help avoid accidental activation or continuation of the XRF analysis by the XRF analyzer 10 allowing XRF analysis only upon activation of the activation switch 13 (by sensing the finger or voice of the user) and the hand sensor 14 sensing the hand of the user.

An indicator light and/or a speaker 19 can be electrically coupled to the electronic processor 17 and can be configured to notify the user upon activation of the XRF analysis. This can further improve XRF analysis safety by alerting the user of the XRF analysis.

The XRF analyzer 10 can also include an interlock switch 16 located at an exterior of the XRF analyzer 10 and electrically coupled to the electronic processor 17 to further improve XRF analysis safety. The interlock switch 16 can be located at an x-ray 22 emission end of the XRF analyzer 10. The interlock switch 16 can be configured to allow activation of the XRF analysis only when the interlock switch 16 is pressed (e.g. against the sample 21). The interlock switch 16 can be combined with the activation switch 13 and/or the hand sensor 14.

Another device on the XRF analyzer 10 to improve XRF analysis safety is a kill switch 15. The kill switch 15 can be located at an exterior of the XRF analyzer 10, electrically coupled to the electronic processor 17, and configured to terminate the XRF analysis when pressed. The kill switch 15 can be located for easy access by the finger or hand of the XRF analyzer 10 user.

In addition, the XRF analyzer 10 can comprise a housing that can include the handle, and can carry the x-ray source 12, the x-ray detector 11, the activation switch 13, the electronic processor 17, the hand sensor 14, the indicator light and/or the speaker 19, the interlock switch 16, and the kill switch 15.

Some or all of the above description, and the following claims, may also be applicable to laser-induced breakdown spectroscopy (LIBS), x-ray diffraction (XRD) analyzers, and Raman spectroscopy tools. The term "XRF analyzer" used herein can be replaced by some or all of the following: LIBS spectrometer, XRD analyzer, Raman spectroscopy equipment, and XRF analyzer.

What is claimed is:
1. An x-ray fluorescence (XRF) analyzer comprising:
   a. an x-ray source configured to emit x-rays towards a sample and an x-ray detector configured to receive fluoresced x-rays emitted from the sample;
   b. an activation switch electrically coupled to an electronic processor and operable to activate an XRF analysis, the XRF analysis including:

i. the electronic processor causing the x-ray source to emit x-rays towards the sample;
  ii. the x-ray detector to receive the fluoresced x-rays emitted from the sample; and
  iii. analysis of the fluoresced x-rays; and
 c. the activation switch including a finger sensor;
 d. the finger sensor comprising a temperature sensor, a photo sensor, a pressure sensor, a capacitive sensor, a radio-frequency identification (RFID) reader configured to receive a signal from an RFID tag on a user of the XRF analyzer, or combinations thereof; and
 e. the finger sensor configured to activate the XRF analysis by a finger of the user approaching or touching the activation switch.

2. The XRF analyzer of claim 1, wherein the finger sensor comprises:
 a. the temperature sensor, the photo sensor, the pressure sensor, the capacitive sensor, or combinations thereof; and
 b. the RFID reader.

3. The XRF analyzer of claim 1, further comprising a hand sensor, and wherein:
 a. the hand sensor is located at a handle of the XRF analyzer and spaced apart from the finger sensor;
 b. the hand sensor comprises a temperature sensor, a photo sensor, a pressure sensor, a capacitive sensor, an RFID reader configured to receive a signal from an RFID tag on the user of the XRF analyzer, or combinations thereof;
 c. the activation switch is configured to activate the XRF analysis only upon:
  i. the finger sensor sensing the finger of the user; and
  ii. the hand sensor sensing a hand of the user.

4. The XRF analyzer of claim 3, wherein the hand sensor comprises:
 a. the temperature sensor, the photo sensor, the pressure sensor, the capacitive sensor, or combinations thereof; and
 b. the RFID reader.

5. The XRF analyzer of claim 1, wherein the finger sensor is the pressure sensor and the pressure sensor is configured to activate the XRF analysis by the finger of the user pressing the pressure sensor with a pressure of between 10 and 30 newtons of force.

6. The XRF analyzer of claim 1, further comprising an indicator light, a speaker, or both electrically coupled to the electronic processor, and wherein the indicator light, the speaker, or both are configured to notify the user upon activation of the XRF analysis.

7. The XRF analyzer of claim 1, further comprising an interlock switch located at an exterior of the XRF analyzer, electrically coupled to the electronic processor, and configured to allow activation of the XRF analysis only when the interlock switch is pressed.

8. The XRF analyzer of claim 1, further comprising a kill switch located at an exterior of the XRF analyzer, electrically coupled to the electronic processor, and configured to terminate the XRF analysis when pressed.

9. The XRF analyzer of claim 1, wherein the finger sensor comprises the pressure sensor, the capacitive sensor, or combinations thereof.

10. The XRF analyzer of claim 1, wherein the activation switch further comprises a microphone configured to receive a verbal command from a user to activate the XRF analysis upon receipt of both the verbal command and activation by the finger sensor.

11. The XRF analyzer of claim 10, wherein the microphone requires a password in the verbal command, includes voice recognition of the user's voice, or both, to activate the XRF analysis.

12. The XRF analyzer of claim 10, wherein the microphone is configured to receive a command from the user to stop the XRF analysis.

13. The XRF analyzer of claim 1, wherein the finger sensor comprises the temperature sensor.

14. The XRF analyzer of claim 1, wherein the finger sensor comprises the photo sensor.

15. The XRF analyzer of claim 1, wherein the finger sensor is configured to activate the XRF analysis by the finger of the user touching the activation switch, and the finger sensor comprises the pressure sensor.

16. The XRF analyzer of claim 15, wherein the finger sensor further comprises the RFID reader.

17. The XRF analyzer of claim 15, wherein the finger sensor further comprises a hand sensor, and wherein:
 a. the hand sensor is located at a handle of the XRF analyzer and spaced apart from the finger sensor;
 b. the hand sensor comprises a temperature sensor, a photo sensor, a pressure sensor, a capacitive sensor, an RFID reader configured to receive a signal from an RFID tag on the user of the XRF analyzer, or combinations thereof;
 c. the activation switch is configured to activate the XRF analysis only upon:
  i. the finger sensor sensing the finger of the user; and
  ii. the hand sensor sensing a hand of the user.

18. The XRF analyzer of claim 1, wherein the finger sensor comprises the capacitive sensor.

19. The XRF analyzer of claim 1, wherein the finger sensor comprises the RFID reader.

* * * * *